US012667537B2

(12) United States Patent
Namkoong et al.

(10) Patent No.: US 12,667,537 B2
(45) Date of Patent: Jun. 30, 2026

(54) PERSONAL CARE COMPOSITIONS COMPRISING CANNABIDIOL AND LICORICE

(71) Applicant: Colgate-Palmolive Company, New York, NY (US)

(72) Inventors: Jin Namkoong, High Bridge, NJ (US); Qiang Wu, Hillsborough, NJ (US); Thomas Boyd, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 377 days.

(21) Appl. No.: 17/301,237

(22) Filed: Mar. 30, 2021

(65) Prior Publication Data

US 2021/0299035 A1 Sep. 30, 2021

Related U.S. Application Data

(60) Provisional application No. 63/002,491, filed on Mar. 31, 2020.

(51) Int. Cl.

| | |
|---|---|
| ***A61K 8/9789*** | (2017.01) |
| ***A61K 8/34*** | (2006.01) |
| ***A61K 8/92*** | (2006.01) |
| ***A61Q 5/02*** | (2006.01) |
| ***A61Q 5/12*** | (2006.01) |
| ***A61Q 15/00*** | (2006.01) |
| ***A61Q 19/00*** | (2006.01) |
| ***A61Q 19/08*** | (2006.01) |
| ***A61Q 19/10*** | (2006.01) |

(52) U.S. Cl.

CPC ............ *A61K 8/9789* (2017.08); *A61K 8/347* (2013.01); *A61K 8/922* (2013.01); *A61Q 5/02* (2013.01); *A61Q 5/12* (2013.01); *A61Q 15/00* (2013.01); *A61Q 19/007* (2013.01); *A61Q 19/08* (2013.01); *A61Q 19/10* (2013.01)

(58) Field of Classification Search

None

See application file for complete search history.

(56) References Cited

U.S. PATENT DOCUMENTS

| | | | |
|---|---|---|---|
| 9,597,279 | B2 | 3/2017 | Nihart |
| 2016/0235661 | A1 | 8/2016 | Changoer et al. |

FOREIGN PATENT DOCUMENTS

| | | |
|---|---|---|
| WO | 2019/234743 | 12/2019 |

OTHER PUBLICATIONS

International Search Report and the Written Opinion of the International Searching Authority issued in International Application PCT/US2021/070334 mailed Jul. 19, 2021.

KHUS+KHUS, 2018, "Copious Body Serum," Mintel Database GNPD AN: 5582071.

*Primary Examiner* — Anna R Falkowitz
*Assistant Examiner* — Garen Gotfredson

(57) ABSTRACT

Disclosed are personal care compositions comprising cannabidiol dissolved in a carrier oil, e.g., hemp seed oil, and licorice extract, wherein the weight ratio of the cannabidiol to the licorice extract is in the range of from 1:6 to 1:40, as well as methods of using these compositions.

6 Claims, 1 Drawing Sheet

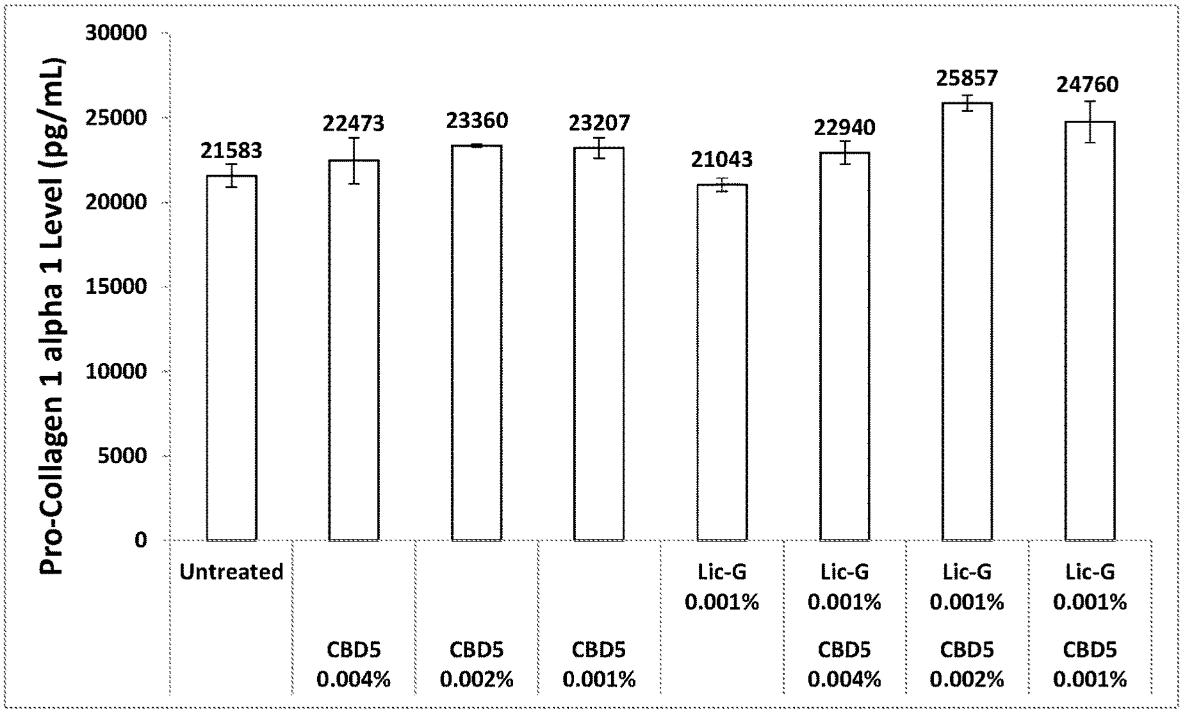
Pro-Collagen 1 alpha 1 Level (pg/mL)
30000
25000
20000
15000
10000
5000
0
21583
22473
23360
23207
21043
22940
25857
24760
Untreated
CBD5 0.004%
CBD5 0.002%
CBD5 0.001%
Lic-G 0.001%
Lic-G 0.001% CBD5 0.004%
Lic-G 0.001% CBD5 0.002%
Lic-G 0.001% CBD5 0.001%

PERSONAL CARE COMPOSITIONS COMPRISING CANNABIDIOL AND LICORICE

BACKGROUND

Cannabidiol (CBD) is a naturally occurring cannabinoid in the *Cannabis sativa* plant, also known as marijuana. Cannabinoids are a class of diverse chemical compounds that act on cannabinoid receptors in cells that alter neurotransmitter release in the brain. There are at least 113 different cannabinoids isolated from *Cannabis*, exhibiting varied effects. While delta-9-tetrahydrocannabinol (THC) is the major active ingredient of *Cannabis* extracts, cannabidiol makes up about 40% of *Cannabis* extracts and has been studied for many different uses. It is known that cannabidiol lacks the psychoactive effects seen in many of the other cannabinoids including delta-9-tetrahydrocannabinol (THC). Cannabidiol has been speculated to have potential as a treatment for a wide range of medical conditions including arthritis, diabetes, alcohol use disorders, multiple sclerosis, chronic pain, schizophrenia, post-traumatic stress disorder (PTSD), depression, rare white matter disorders, antibiotic-resistant infections, epilepsy, inflammation, and other neurological disorders. CBD has also generally been found to possess potent antibacterial properties, anxiolytic, and anti-inflammatory properties.

In recent years, medicinal and therapeutic uses of cannabinoids have garnered increased attention in both the media and within the scientific community. In the United States, *cannabis* laws have become steadily more liberal, with many states permitting the use of cannabinoids for medical purposes or for general recreational use. As public support grows, the numbers of these states are likely to increase and therefore support the efforts to clarify the potential therapeutic benefits of medical *cannabis* on various health outcomes. Cannabidiol is a trendy ingredient in the personal care industry currently.

Pro-Collagen 1 alpha 1 (COL1A1) is a Type I collagen. It is one of the main extracellular matrix proteins in skin and other connective tissues and gives the skin rigidity and firmness. As people age, collagen synthesis is reduced. Therefore, collagen is widely used as a biomarker to evaluate skin firmness.

It is therefore desirable to develop and formulate personal care products that boost pro-collagen 1 synthesis in skin.

BRIEF SUMMARY

In one aspect, the invention provides a personal care composition comprising cannabidiol dissolved in a carrier oil, e.g., hemp seed oil, and licorice extract, wherein the weight ratio of the cannabidiol to the licorice extract is in the range of from 1:6 to 1:40. In some embodiments, the weight ratio of the cannabidiol to the licorice extract is in the range of from 1:6 to 1:35, from 1:6 to 1:30, from 1:6 to 1:25, from 1:6 to 1:20, from 1:8 to 1:35, from 1:8 to 1:30, from 1:8 to 1:25, from 1:8 to 1:20, from 1:10 to 1:35, from 1:10 to 1:30, from 1:10 to 1:25, or from 1:10 to 1:20.

In some embodiments, the cannabidiol is present in an amount of from 0.00005% to 0.5%, from 0.00005% to 0.25%, from 0.00005% to 0.1%, from 0.00005% to 0.05%, from 0.00005% to 0.01%, from 0.00005% to 0.005%, from 0.00005% to 0.001%, from 0.00005% to 0.0005%, from 0.00005% to 0.0001%, from 0.0001% to 0.5%, from 0.00001% to 0.25%, from 0.0001% to 0.1%, from 0.0001% to 0.05%, from 0.0001% to 0.01%, from 0.0001% to 0.005%, from 0.0001% to 0.001%, from 0.0001% to 0.0005%, from 0.0005% to 0.5%, from 0.0005% to 0.25%, from 0.0005% to 0.1%, from 0.0005% to 0.05%, from 0.0005% to 0.01%, from 0.0005% to 0.005%, from 0.0005% to 0.001%, from 0.001% to 0.5%, from 0.001% to 0.25%, from 0.001% to 0.1%, from 0.001% to 0.05%, from 0.001% to 0.01%, from 0.001% to 0.005%, from 0.005% to 0.5%, from 0.005% to 0.25%, from 0.005% to 0.1%, from 0.005% to 0.05%, from 0.005% to 0.01%, from 0.01% to 0.5%, from 0.01% to 0.25%, from 0.01% to 0.1%, from 0.01% to 0.05%, from 0.05% to 0.5%, from 0.05% to 0.25%, from 0.05% to 0.1%, from 0.1% to 0.5%, from 0.1% to 0.25%, by weight of the composition.

In some embodiments, the licorice extract is present in an amount of from 0.0005% to 10%, from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 10%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.003% to 10%, from 0.003% to 5%, from 0.003% to 1%, from 0.003% to 0.5%, from 0.003% to 0.1%, from 0.003% to 0.05%, from 0.003% to 0.01%, from 0.003% to 0.005%, from 0.005% to 10%, from 0.005% to 5%, from 0.005% to 1%, from 0.005% to 0.5%, from 0.005% to 0.1%, from 0.005% to 0.05%, from 0.005% to 0.01%, from 0.01% to 10%, from 0.01% to 5%, from 0.01% to 1%, from 0.01% to 0.5%, from 0.01% to 0.1%, from 0.01% to 0.05%, from 0.05% to 10%, from 0.05% to 5%, from 0.05% to 1%, from 0.05% to 0.5%, from 0.05% to 0.1%, from 0.1% to 10%, from 0.1% to 5%, from 0.1% to 1%, from 0.1% to 0.5%, from 0.5% to 10%, from 0.5% to 5%, or from 0.5% to 1% by weight of the composition. In some embodiments, the carrier oil is present in an amount of from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.005% to 5%, from 0.005% to 1%, from 0.005% to 0.5%, from 0.005% to 0.1%, from 0.005% to 0.05%, from 0.005% to 0.01%, from 0.01% to 5%, from 0.01% to 1%, from 0.01% to 0.5%, from 0.01% to 0.1%, from 0.01% to 0.05%, from 0.05% to 5%, from 0.05% to 1%, from 0.05% to 0.5%, from 0.05% to 0.1%, from 0.1% to 5%, from 0.1% to 1%, from 0.1% to 0.5%, from 0.5% to 5%, or from 0.5% to 1% by weight of the composition. In some embodiments, the carrier oil is selected from hemp seed oil, *Cannabis sativa* seed oil, coconut oil, palm oil, olive oil, jojoba oil, argan oil, and mineral oil. In some embodiments, the carrier oil is selected from hemp seed oil, *Cannabis sativa* seed oil and coconut oil. In some embodiments, the carrier oil is hemp seed oil.

In another aspect, the invention provides a method of increasing pro-collagen 1 (e.g., Pro-Collagen 1a1) expression in skin, comprising applying an effective amount of a personal care composition comprising cannabidiol dissolved in a carrier oil, e.g., hemp seed oil, and licorice extract, e.g., any of personal care compositions as disclosed herein, to the skin of a subject in need thereof, wherein the weight ratio of the cannabidiol to the licorice extract is in the range of from 1:6 to 1:40.

In another aspect, the invention provides the use of cannabidiol dissolved in a carrier oil, e.g., hemp seed oil, and licorice extract in the manufacture of a personal care composition, e.g., any of personal care compositions as disclosed herein, for increasing pro-collagen 1 (e.g., Pro-Collagen 1a1) expression in skin, wherein the weight ratio of the cannabidiol to the licorice extract is in the range of from 1:6 to 1:40.

In another aspect, the invention provides the use of cannabidiol dissolved in a carrier oil, e.g., hemp seed oil, and licorice extract in a personal care composition, e.g., any of personal care compositions as disclosed herein, for increasing pro-collagen 1 (e.g., Pro-Collagen 1a1) expression in skin, wherein the weight ratio of the cannabidiol to the licorice extract is in the range of from 1:6 to 1:40.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The present invention will become more fully understood from the detailed description and the accompanying drawings.

FIG. 1 shows a graph of Pro-Collagen 1α1 level secreted from fibroblast cells treated with CBD5 (0.001%, 0.002% or 0.004%) and/or Lic-G (0.001%).

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. The amounts given are based on the active weight of the material.

In the present invention, it has been found that the treatment of cannabidiol dissolved in a carrier oil increases Pro-Collagen 1α1 expression in fibroblast cells. It has been further found that although licorice extract alone does not increase Pro-Collagen 1α1 expression in fibroblast cells, the co-treatment of Licorice extract together with cannabidiol at certain ratios shows synergy impact on boosting Pro-Collagen 1α1 expression. Thus, Licorice extract together with cannabidiol at certain ratios may be used in personal care products to boost pro-collagen 1α1 synthesis in skin.

The present invention provides, in an aspect, a personal care composition (Composition 1.0), e.g., skin care composition, comprising cannabidiol dissolved in a carrier oil, e.g., hemp seed oil, and licorice extract, wherein the weight ratio of the cannabidiol to the licorice extract is in the range of from 1:6 to 1:40.

For example, the invention includes:

- 1.1 Composition 1.0, wherein the weight ratio of the cannabidiol to the licorice extract is in the range of from 1:6 to 1:35, from 1:6 to 1:30, from 1:6 to 1:25, from 1:6 to 1:20, from 1:8 to 1:35, from 1:8 to 1:30, from 1:8 to 1:25, from 1:8 to 1:20, from 1:10 to 1:35, from 1:10 to 1:30, from 1:10 to 1:25, or from 1:10 to 1:20, optionally wherein the weight ratio of the cannabidiol to the licorice extract is in the range of from 1:10 to 1:20.
- 1.2 Any of the preceding compositions, wherein the cannabidiol is present in an amount of from 0.00005% to 0.5%, from 0.00005% to 0.25%, from 0.00005% to 0.1%, from 0.00005% to 0.05%, from 0.00005% to 0.01%, from 0.00005% to 0.005%, from 0.00005% to 0.001%, from 0.00005% to 0.0005%, from 0.00005% to 0.0001%, from 0.0001% to 0.5%, from 0.0001% to 0.25%, from 0.0001% to 0.1%, from 0.0001% to 0.05%, from 0.0001% to 0.01%, from 0.0001% to 0.005%, from 0.0001% to 0.001%, from 0.0001% to 0.0005%, from 0.0005% to 0.5%, from 0.0005% to 0.25%, from 0.0005% to 0.1%, from 0.0005% to 0.05%, from 0.0005% to 0.01%, from 0.0005% to 0.005%, from 0.0005% to 0.001%, from 0.001% to 0.5%, from 0.001% to 0.25%, from 0.001% to 0.1%, from 0.001% to 0.05%, from 0.001% to 0.01%, from 0.001% to 0.005%, from 0.005% to 0.5%, from 0.005% to 0.25%, from 0.005% to 0.1%, from 0.005% to 0.05%, from 0.005% to 0.01%, from 0.01% to 0.5%, from 0.01% to 0.25%, from 0.01% to 0.1%, from 0.01% to 0.05%, from 0.05% to 0.5%, from 0.05% to 0.25%, from 0.05% to 0.1%, from 0.1% to 0.5%, from 0.1% to 0.25%, by weight of the composition, optionally wherein the cannabidiol is present in an amount of from 0.0005% to 0.25% by weight of the composition.
- 1.3 Any of the preceding compositions, wherein the licorice extract is present in an amount of from 0.0005% to 10%, from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 10%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.003% to 10%, from 0.003% to 5%, from 0.003% to 1%, from 0.003% to 0.5%, from 0.003% to 0.1%, from 0.003% to 0.05%, from 0.003% to 0.01%, from 0.003% to 0.005%, from 0.005% to 10%, from 0.005% to 5%, from 0.005% to 1%, from 0.005% to 0.5%, from 0.005% to 0.1%, from 0.005% to 0.05%, from 0.005% to 0.01%, from 0.01% to 10%, from 0.01% to 5%, from 0.01% to 1%, from 0.01% to 0.5%, from 0.01% to 0.1%, from 0.01% to 0.05%, from 0.05% to 10%, from 0.05% to 5%, from 0.05% to 1%, from 0.05% to 0.5%, from 0.05% to 0.1%, from 0.1% to 10%, from 0.1% to 5%, from 0.1% to 1%, from 0.1% to 0.5%, from 0.5% to 10%, from 0.5% to 5%, or from 0.5% to 1% by weight of the composition, optionally wherein the licorice extract is present in an amount of from 0.003% to 5% by weight of the composition.
- 1.4 Any of the preceding compositions, wherein the carrier oil is present in an amount of from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.005% to 5%, from 0.005% to 1%, from 0.005% to 0.5%, from 0.005% to 0.1%, from 0.005% to 0.05%, from 0.005% to 0.01%, from 0.01% to 5%, from 0.01% to 1%, from 0.01% to 0.5%, from 0.01% to 0.1%, from 0.01% to 0.05%, from 0.05% to 5%, from 0.05% to 1%, from 0.05% to 0.5%, from 0.05% to 0.1%, from 0.1% to 5%, from 0.1% to 1%, from 0.1% to 0.5%, from 0.5% to 5%, or from 0.5% to 1% by weight of the composition, optionally wherein the carrier oil is present in an amount of from 0.01% to 5% by weight of the composition.

1.5 Any of the preceding compositions, wherein the carrier oil is selected from hemp seed oil, *Cannabis sativa* seed oil, coconut oil, palm oil, olive oil, jojoba oil, argan oil, and mineral oil, optionally wherein the carrier oil is selected from hemp seed oil, *Cannabis sativa* seed oil and coconut oil, further optionally wherein the carrier oil is hemp seed oil.

1.6 Any of the preceding compositions, wherein the composition comprises a cosmetically acceptable base suitable for application to the skin, e.g., a cosmetically acceptable base comprising one or more of water-soluble alcohols (such as $C_{2-8}$ alcohols including ethanol); glycols (including propylene glycol, dipropylene glycol, tripropylene glycol and mixtures thereof); glycerides (including mono-, di- and triglycerides); medium to long chain organic acids, alcohols and esters; surfactants (including emulsifying and dispersing agents); additional amino acids; structurants (including thickeners and gelling agents, for example polymers, silicates and silicon dioxide); emollients; fragrances; and colorants (including dyes and pigments).

1.7 Any of the preceding compositions, further comprising a soothing agent.

1.8 Composition 1.7, wherein the soothing agent is selected from Aloe vera, allantoin, D-panthenol, turmeric, avocado oil and other vegetative oils, and lichen extract.

1.9 Any of the preceding compositions, further comprising a fragrance component.

1.10 Any of the preceding compositions, further comprising an antiperspirant active ingredient.

1.11 Composition 1.10, wherein the antiperspirant active ingredient is a metal-containing antiperspirant active ingredient containing aluminum, magnesium, strontium, zirconium, zinc or a combination thereof.

1.12 Composition 1.11, wherein the metal-containing antiperspirant active ingredient is present in an amount of 1 to 40% by weight of the composition, optionally from 6, 7, 8, 9, 10, 11, 12, 13, or 14% up to 40% by weight of the composition, or, optionally, 10 to 30%, 11 to 25%, 12 to 20%, 13 to 15%, 14 to 20%, 15 to 20%, 11 to 15%, or 12 to 14% by weight of the composition.

1.13 Any of the preceding compositions, wherein the composition comprises water in an amount from about 10-75 wt. %, e.g. 20-60 wt. % based on total weight of the composition.

1.14 Any of the preceding compositions, wherein the composition is substantially anhydrous, e.g., comprises less than 5% water.

1.15 Any of the preceding compositions, wherein the composition is completely anhydrous, i.e., comprises 0% water.

1.16 Any of the preceding compositions, wherein the composition is an oil-in-water (O/W) emulsion or a water-in-oil emulsion (W/O).

1.17 Any of the preceding compositions, wherein the composition comprises an oil phase.

1.18 Composition 1.17, wherein the oil phase comprises soybean oil, castor oil, palm kernel oil or combinations thereof.

1.19 Any of the preceding compositions, wherein the composition is a lotion, a serum, a toner, a body wash, a shower gel, a bar soap, a liquid hand soap, a shampoo, a body cream, a hair conditioner, an antiperspirant and/or deodorant, e.g., an antiperspirant stick, an aerosol antiperspirant spray, or a liquid roll-on antiperspirant.

1.20 Any of the preceding compositions, wherein the cannabidiol is present in an amount of from 0.0005% to 0.25%, the licorice extract is present in an amount of from 0.003% to 5%, and the carrier oil, e.g., hemp seed oil, is present in an amount of from 0.01% to 5% by weight of the composition.

1.21 Any of the preceding compositions for use in increasing pro-collagen 1 (e.g., Pro-Collagen 1α1) expression in skin.

The personal care composition of the invention comprises cannabidiol dissolved in a carrier oil. The structure of CBD is shown below:

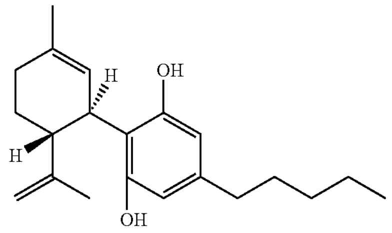

cannabidiol

In some embodiments, the cannabidiol is present in an amount of from 0.00005% to 0.5%, from 0.00005% to 0.25%, from 0.00005% to 0.1%, from 0.00005% to 0.05%, from 0.00005% to 0.01%, from 0.00005% to 0.005%, from 0.00005% to 0.001%, from 0.00005% to 0.0005%, from 0.00005% to 0.0001%, from 0.0001% to 0.5%, from 0.00001% to 0.25%, from 0.0001% to 0.1%, from 0.0001% to 0.05%, from 0.0001% to 0.01%, from 0.0001% to 0.005%, from 0.0001% to 0.001%, from 0.0001% to 0.0005%, from 0.0005% to 0.5%, from 0.0005% to 0.25%, from 0.0005% to 0.1%, from 0.0005% to 0.05%, from 0.0005% to 0.01%, from 0.0005% to 0.005%, from 0.0005% to 0.001%, from 0.001% to 0.5%, from 0.001% to 0.25%, from 0.001% to 0.1%, from 0.001% to 0.05%, from 0.001% to 0.01%, from 0.001% to 0.005%, from 0.005% to 0.5%, from 0.005% to 0.25%, from 0.005% to 0.1%, from 0.005% to 0.05%, from 0.005% to 0.01%, from 0.01% to 0.5%, from 0.01% to 0.25%, from 0.01% to 0.1%, from 0.01% to 0.05%, from 0.05% to 0.5%, from 0.05% to 0.25%, from 0.05% to 0.1%, from 0.1% to 0.5%, from 0.1% to 0.25%, by weight of the composition. In some embodiments, the cannabidiol is present in an amount of from 0.0005% to 0.25% by weight of the composition.

Any known carrier oils may be used to dissolve and dilute cannabidiol. The carrier oil may be selected from hemp seed oil, *Cannabis sativa* seed oil, coconut oil, palm oil, olive oil, jojoba oil, argan oil, and mineral oil. In some embodiments, the carrier oil is selected from hemp seed oil, *Cannabis sativa* seed oil and coconut oil. In some embodiments, the carrier oil is hemp seed oil. In some embodiments, the carrier oil is present in an amount of from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.005% to 5%, from 0.005% to 1%, from 0.005% to 0.5%, from 0.005% to 0.1%, from 0.005% to 0.05%, from 0.005% to 0.01%, from 0.01% to 5%, from 0.01% to 1%, from 0.01% to 0.5%, from 0.01% to 0.1%, from 0.01% to 0.05%, from 0.05% to 5%, from 0.05% to 1%, from 0.05% to 0.5%, from 0.05% to 0.1%, from 0.1% to 5%, from 0.1% to 1%, from 0.1% to 0.5%, from 0.5% to 5%, or from 0.5% to 1% by weight of the composition. In some embodiments, the carrier oil is present in an amount of from 0.01 to 5% by weight of the composition. In this disclosure, the amount of the carrier oil includes the amount of cannabidiol dissolved in the carrier oil. In some embodiments, the concentration of cannabidiol dissolved in the carrier oil may be from 0.5% to 10%, from 1% to 5%, about 1%, or about 5% by weight of the carrier oil.

The personal care composition of the invention comprises licorice extract. Licorice extract is an extract from the *Glycyrrhiza glabra* plant which contains glycyrrhizic acid or GZA. In some embodiments, the licorice extract is present in an amount of from 0.0005% to 10%, from 0.0005% to 5%, from 0.0005% to 1%, from 0.0005% to 0.5%, from 0.0005% to 0.1%, from 0.0005% to 0.05%, from 0.0005% to 0.01%, from 0.0005% to 0.005%, from 0.0005% to 0.001%, from 0.001% to 10%, from 0.001% to 5%, from 0.001% to 1%, from 0.001% to 0.5%, from 0.001% to 0.1%, from 0.001% to 0.05%, from 0.001% to 0.01%, from 0.001% to 0.005%, from 0.003% to 10%, from 0.003% to 5%, from 0.003% to 1%, from 0.003% to 0.5%, from 0.003% to 0.1%, from 0.003% to 0.05%, from 0.003% to 0.01%, from 0.003% to 0.005%, from 0.005% to 10%, from 0.005% to 5%, from 0.005% to 1%, from 0.005% to 0.5%, from 0.005% to 0.1%, from 0.005% to 0.05%, from 0.005% to 0.01%, from 0.01% to 10%, from 0.01% to 5%, from 0.01% to 1%, from 0.01% to 0.5%, from 0.01% to 0.1%, from 0.01% to 0.05%, from 0.05% to 10%, from 0.05% to 5%, from 0.05% to 1%, from 0.05% to 0.5%, from 0.05% to 0.1%, from 0.1% to 10%, from 0.1% to 5%, from 0.1% to 1%, from 0.1% to 0.5%, from 0.5% to 10%, from 0.5% to 5%, or from 0.5% to 1% by weight of the composition. In some embodiments, the licorice extract is present in an amount of from 0.003% to 5% by weight of the composition. Licorice dry extract may be added into the personal care composition. Alternatively, Licorice extract may be first dissolved and diluted in a solvent, e.g., glycerin, and then the licorice extract solution may be added into the personal care composition. When the licorice extract solution is used, the amount of the licorice extract, in this disclosure, means the amount of licorice extract contained in the solution. In other words, the amount of licorice extract does not include the amount of solvent, e.g., glycerin, used to dilute licorice extract.

The weight ratio of the cannabidiol to the licorice extract in the personal care composition of the invention may be in the range of from 1:6 to 1:40. In some embodiments, the weight ratio of the cannabidiol to the licorice extract is in the range of from 1:6 to 1:35, from 1:6 to 1:30, from 1:6 to 1:25, from 1:6 to 1:20, from 1:8 to 1:35, from 1:8 to 1:30, from 1:8 to 1:25, from 1:8 to 1:20, from 1:10 to 1:35, from 1:10 to 1:30, from 1:10 to 1:25, or from 1:10 to 1:20.

The composition may be any type of personal care composition. In certain embodiments, the composition is any composition that can be formulated into topical skin care formulations suitable for application to skin. Examples of such compositions include, but are not limited to, personal care compositions, skin care compositions, antiperspirants, deodorants, body washes, creams, shower gels, bar soaps, shampoo, hair conditioners, and cosmetics. The composition may be leave-on (lotion, serum, toner etc.) or rinse off (bar soap, liquid hand soap, shower gel, etc.) products. The composition can comprise a single phase or can be a multi-phase system, for example a system comprising a polar phase and an oil phase, optionally in the form of a stable emulsion. The composition can be liquid, semi-solid or solid. The formulation can be provided in any suitable container such as an aerosol can, tube or container with a porous cap, roll-on container, bottle, container with an open end, etc.

Optional ingredients that may be included in the personal care composition of the invention include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments.

The composition may also optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$ alkyl benzoate. The non-volatile silicone material can be a polyethersiloxane, polyalkyarylsiloxane or polyethersiloxane copolymer. An illustrative non-volatile silicone material is phenyl trimethicone. Examples include, but are not limited to, PPG-14 butyl ether, PPG-3 myristyl ether, secondary alcohol ethoxylates (e.g. Tergitol sold by Dow Chemical Company, Midland, MI) stearyl alcohol, stearic acid and salts thereof, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The personal care composition may comprise additional antiperspirant actives. The additional active antiperspirant ingredient may be selected from aluminum salts, zirconium salts and zinc salts. In some embodiment, the personal care composition may comprise an aluminum containing antiperspirant active. Any of the known aluminum containing antiperspirant active materials can be utilized in the composition. Aluminum containing antiperspirant actives include, but are not limited to, aluminum chlorohydrate, aluminum chloride, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum, sesquichlorohydrate polyethylene glycol, aluminum sesquichlorohydrate propylene glycol.

The personal care composition may include any known deodorant active. Examples of deodorant actives include, but are not limited to, antimicrobial actives, alcohols, 2,4, 4'-trichloro-2'-hydroxy diphenyl ether (Triclosan), benzethonium chloride, polyhexamethylene biguanides, triethylcitrate, 2-amino-2-methyl-1-propanol (AMP), cetyltrimethylammomium bromide, cetyl pyridinium chloride, farnesol (3,7, 1 1-trimethyl-2,6,10-dodecatrien-1-ol), N-(4-chlorophenyl)-N'-(3,4-dichlorophenyl) urea (Triclocarban), silver halides, octoxyglycerin (Sensiva™ SC 50) and various zinc salts (for example, zinc ricinoleate), bactericides, and/or bacteriostats. The deodorant active can be included in the composition in an amount of 0-5%, or 0.01-1% by weight, of the total weight of the composition. Triclosan can be included in an amount of 0.05% to 0.5% by weight, of the total weight of the composition.

Gelling agents may be included in the personal care composition. Examples of gelling agents include, but are not limited to, waxes, esters of fatty acid and fatty alcohol, triglycerides, partially or fully hydrogenated soybean oil, partially or fully hydrogenated castor oil, other partial or fully hydrogenated plant oils, stearyl alcohol, or other cosmetically acceptable materials, which are solid or semi-solid at room temperature and provide a consistency suitable for application to the skin.

Antioxidants may be added to the composition, preferably to act as ingredient protectants and for maintenance of long-term stability of the composition. Examples of antioxidants include, but are not limited to citric acid, butylated hydroxytoluene, pentaerythrityl tetra-di-t-butyl hydroxyhydrocinnamate.

The composition may also contain polymeric materials for thickening, such as polyamides, cellulose derivatives (e.g., hydroxypropylcellulose, hydroxypropyl methyl cellulose, etc.) and natural or synthetic gums, such as polyglycerides including agar, agarose, pectin, or guars or mixtures or combinations thereof. One class of materials worthy of attention for thickening a water-immiscible phase comprises derivatives of hydrolysed starch or other polysaccharides, including in particular esterified dextrins, such as dextrin palmitate. A further class of polymers that is particularly directed to structuring an oil phase containing a silicone oil comprises polysiloxane elastomers. Suspending agents such as silicas or clays such as bentonite, montmorillonite or hectorite, including those available under the trademark Bentone can also be employed to thicken liquid compositions according to the invention. The composition can be thickened with non-polymeric organic gellants, including selected dibenzylidene alditols (eg dibenzylidene sorbitol).

Fragrance may be included in the personal care composition. Any fragrance suitable for personal care use may be incorporated into the personal care composition of the invention. Fragrances tend to be relatively volatile aroma compounds which are capable of entering the gas phase at skin surface temperature.

The personal care compositions of the invention may be manufactured using methods known in the art. Typically, the ingredients are combined and optionally heated where components need to be melted. The components are mixed. Desirably, volatile materials such as fragrant materials are incorporated in the composition in the latter stages of a mixing cycle in order to avoid volatilization thereof. After mixing, the composition may be poured directly into the dispensers and the container capped to preserve the product until use.

In another aspect, the invention provides a method of increasing pro-collagen 1 (e.g., Pro-Collagen 1α1) expression in skin, comprising applying an effective amount of a personal care composition comprising cannabidiol dissolved in in a carrier oil, e.g., hemp seed oil, and licorice extract, e.g., any of personal care compositions as disclosed herein, e.g., any of Compositions 1 et seq., to the skin of a subject in need thereof, wherein the weight ratio of the cannabidiol to the licorice extract is in the range of from 1:6 to 1:40.

In another aspect, the invention provides the use of cannabidiol dissolved in a carrier oil, e.g., hemp seed oil, and licorice extract in the manufacture of a personal care composition, e.g., any of personal care compositions as disclosed herein, e.g., any of Compositions 1 et seq., for increasing increase pro-collagen 1 (e.g., Pro-Collagen 1α1) expression in skin, wherein the weight ratio of the cannabidiol to the licorice extract is in the range of from 1:6 to 1:40.

In another aspect, the invention provides the use of cannabidiol dissolved in a carrier oil, e.g., hemp seed oil, and licorice extract in a personal care composition, e.g., any of personal care compositions as disclosed herein, e.g., any of Compositions 1 et seq., for increasing pro-collagen 1 (e.g., Pro-Collagen 1α1) expression in skin, wherein the weight ratio of the cannabidiol to the licorice extract is in the range of from 1:6 to 1:40.

EXAMPLES

Example 1

In order to examine the effect of cannabidiol and licorice extract on Pro-Collagen 1α1 expression, In vitro studies were conducted on a human fibroblast cell model. Cannabidiol and licorice extract solutions were prepared as follows.

Stock Solutions:

1% CDB5 was prepared by diluting CBD (5%) in Hemp Seed oil in 100% DMSO (1:100). 12.5% Licorice-Glycerin extract was prepared by making 25% Licorice extract in 100% Ethanol (w/v) and further diluting it 1:2 in 100% Glycerin.

0.4% Lic-G is prepared by diluting 16 uL 12.5% in 484 uL Media.

Dilutions:

2× solutions

CBD5 0.008%: 160 uL 1% CBD5+19.842 mL Media

CBD5 0.004%: 10 mL CBD5 0.008%+10 mL Media

CBD5 0.002%: 10 mL CBD5 0.004%+10 mL Media

Lic-G 0.002%: 50 uL Lic-G 0.4%+9.95 mL Media

Fibroblast cells were plated on 24-well plates. Right before the treatment, the CBD and Licorice extract solutions were mixed to make the final concentrations as shown in Table 1. For combination treatment, 2× solutions of CBD and Licorice extract were mixed. For single treatment, 2× solutions were mixed with the equal volume of media.

TABLE I

| List of test samples | | |
|---|---|---|
| Test Sample | | Description |
| Untreated | | Media alone |
| CBD5 0.004% | | CBD (5%) 0.004% in untreated media |
| CBD5 0.002% | | CBD (5%) 0.002% in untreated media |
| CBD5 0.001% | | CBD (5%) 0.001% in untreated media |
| | Lic-G 0.001% | Licorice-Glycerin 0.001% in Media |
| CBD5 0.004% | Lic-G 0.001% | CBD (5%) 0.004% and Licorice-Glycerin 0.001% in Media |
| CBD5 0.002% | Lic-G 0.001% | CBD (5%) 0.002% and Licorice-Glycerin 0.001% in Media |
| CBD5 0.001% | Lic-G 0.001% | CBD (5%) 0.001% and Licorice-Glycerin 0.001% in Media |

0.5 ml of each test sample was directly applied to the 24-well plates in triplicates and the fibroblast cultures were incubated for 24 hours. On the following data, culture media was collected and stored in −20° C. The samples of media were diluted (1:100) and the level of Pro-Collagen 1α1 released in culture media was quantified with an ELISA kit according to the instruction of Pro-Collagen 1α1 DuoSet ELISA (R&D Systems). The results are shown in Table 2. All results were average of 3 replicas. The bar graph of the results is displayed in FIG. 1.

TABLE 2

| Pro-Collagen 1α1 from cell treatment | | | | | | | | |
|---|---|---|---|---|---|---|---|---|
| | Untreated | CBD5 0.004% | CBD5 0.002% | CBD5 0.001% | Lic-G 0.001% | CBD5 0.004% Lic-G 0.001% | CBD5 0.002% Lic-G 0.001% | CBD5 0.001% Lic-G 0.001% |
| Pro-Collagen 1 (pg/mL) | 21583 | 22473 | 23360 | 23207 | 21043 | 22940 | 25857 | 24760 |
| Change from Untreated | 0 | 890 | 1777 | 1623 | −540 | 1357 | 4273 | 3177 |

As shown in Table 2 and FIG. 1, the treatment of CBD5 (5% cannabidiol dissolved in hemp seed oil) at all concentrations tested (0.001%, 0.002% and 0.004% CBD5) increased Pro-Collagen 1α1 expression, while Licorice extract alone (0.001% Lic-G) did not increase Pro-Collagen 1α1 expression. The co-treatment of Licorice extract (0.001% Lic-G) together with CBD5 at two concentrations tested (0.001% and 0.002% CBD5) showed synergy impact on boosting Pro-Collagen 1α1 expression. However, at the higher concentration of CBD5 (0.004% CBD5), no synergy was observed. This result demonstrates that the combination of cannabidiol in hemp seed oil and licorice extract in certain ratios delivers synergetic benefits to boost pro-collagen I synthesis.

The present disclosure has been described with reference to exemplary embodiments. Although a limited number of embodiments have been shown and described, it will be appreciated by those skilled in the art that changes may be made in these embodiments without departing from the principles and spirit of the preceding detailed description. It is intended that the present disclosure be construed as including all such modifications and alterations insofar as they come within the scope of the appended claims or the equivalents thereof.

What is claimed is:

1. A personal care composition comprising cannabidiol dissolved in a carrier oil; and licorice extract, comprising effective amounts of the cannabidiol and the licorice extract;
- wherein the cannabidiol is present in an amount of from 0.00005% to 0.00016% by weight of the composition;
- wherein the licorice extract is present in an amount of 0.001% by weight of the composition; and
- wherein the carrier oil is hemp seed oil.

2. The personal care composition of claim 1, wherein the carrier oil is present in an amount of from 0.0005% to 5% by weight of the composition.

3. The personal care composition of claim 1, in a cosmetically acceptable base suitable for application to the skin, the base comprising one or more of water-soluble alcohols; glycols; glycerides; medium to long chain organic acids, alcohols and esters; surfactants; additional amino acids; structurants; emollients; fragrances; soothing agents; and colorants.

4. The personal care composition of claim 1, wherein the carrier oil is present in an amount of from 0.01% to 5% by weight of the composition.

5. The personal care composition of claim 1, wherein the composition is a lotion, a serum, a toner, a body wash, a shower gel, a bar soap, a liquid hand soap, a body cream, a shampoo, a hair conditioner, an antiperspirant or a deodorant.

6. A method of increasing pro-collagen 1 expression in skin, comprising applying an effective amount of a personal care composition comprising cannabidiol dissolved in a carrier oil and licorice extract to the skin of a subject in need thereof,
- wherein the cannabidiol is present in an amount of from 0.00005% to 0.00016% by weight of the composition; and
- wherein the licorice extract is present in an amount of 0.001% by weight of the composition; and
- wherein the carrier oil is hemp seed oil.

* * * * *